(12) United States Patent
Jarvik

(10) Patent No.: US 7,479,102 B2
(45) Date of Patent: Jan. 20, 2009

(54) MINIMALLY INVASIVE TRANSVALVULAR VENTRICULAR ASSIST DEVICE

(76) Inventor: Robert Jarvik, 333 W. 52nd St., New York, NY (US) 10019

( * ) Notice: Subject to any disclaimer, the term of this patent is extended or adjusted under 35 U.S.C. 154(b) by 720 days.

(21) Appl. No.: 11/078,559

(22) Filed: Feb. 28, 2005

(65) Prior Publication Data

US 2006/0195004 A1 Aug. 31, 2006

(51) Int. Cl.
*A61M 1/12* (2006.01)
(52) U.S. Cl. ...................................................... 600/16
(58) Field of Classification Search ............. 600/16–18; 623/2.17, 2.31, 2.33
See application file for complete search history.

(56) References Cited

U.S. PATENT DOCUMENTS

| | | | | |
|---|---|---|---|---|
| 4,588,404 A | * | 5/1986 | Lapeyre | 623/3.21 |
| 4,625,712 A | | 12/1986 | Wampler | |
| 4,906,229 A | * | 3/1990 | Wampler | 600/16 |
| 4,919,647 A | | 4/1990 | Nash | |
| 4,994,017 A | | 2/1991 | Yozu | |
| 5,169,378 A | * | 12/1992 | Figuera | 600/16 |
| 5,222,980 A | * | 6/1993 | Gealow | 623/3.12 |
| 5,290,227 A | | 3/1994 | Pasque | |
| 5,318,595 A | * | 6/1994 | Ferek-Petric et al. | 607/17 |
| 5,888,241 A | * | 3/1999 | Jarvik | 600/16 |
| 5,928,132 A | * | 7/1999 | Leschinsky | 600/16 |
| 5,964,694 A | * | 10/1999 | Siess et al. | 600/17 |
| 6,083,260 A | * | 7/2000 | Aboul-Hosn | 623/3.14 |
| 6,132,364 A | * | 10/2000 | Rottenberg et al. | 600/16 |
| 6,136,025 A | | 10/2000 | Barbut et al. | |
| 6,176,848 B1 | | 1/2001 | Rau | |
| 2004/0044266 A1 | * | 3/2004 | Siess et al. | 600/16 |

* cited by examiner

*Primary Examiner*—Carl H Layno
*Assistant Examiner*—Jonathan B Thomas

(57) ABSTRACT

A tiny electrically powered hydrodynamic blood pump is disclosed which occupies one third of the aortic or pulmonary valve position, and pumps directly from the left ventricle to the aorta or from the right ventricle to the pulmonary artery. The device is configured to exactly match or approximate the space of one leaflet and sinus of valsalva, with part of the device supported in the outflow tract of the ventricular cavity adjacent to the valve. In the configuration used, two leaflets of the natural tri-leaflet valve remain functional and the pump resides where the third leaflet had been. When implanted, the outer surface of the device includes two faces against which the two valve leaflets seal when closed. To obtain the best valve function, the shape of these faces may be custom fabricated to match the individual patient's valve geometry based on high resolution three dimensional CT or MRI images. Another embodiment of the invention discloses a combined two leaflet tissue valve with the miniature blood pump supported in the position usually occupied by the third leaflet. Either stented or un-stented tissue valves may be used. This structure preserves two thirds of the valve annulus area for ejection of blood by the natural ventricle, with excellent washing of the aortic root and interface of the blood pump to the heart. In the aortic position, the blood pump is positioned in the non-coronary cusp. A major advantage of the transvalvular VAD is the elimination of both the inflow and outflow cannulae usually required with heart assist devices.

14 Claims, 2 Drawing Sheets

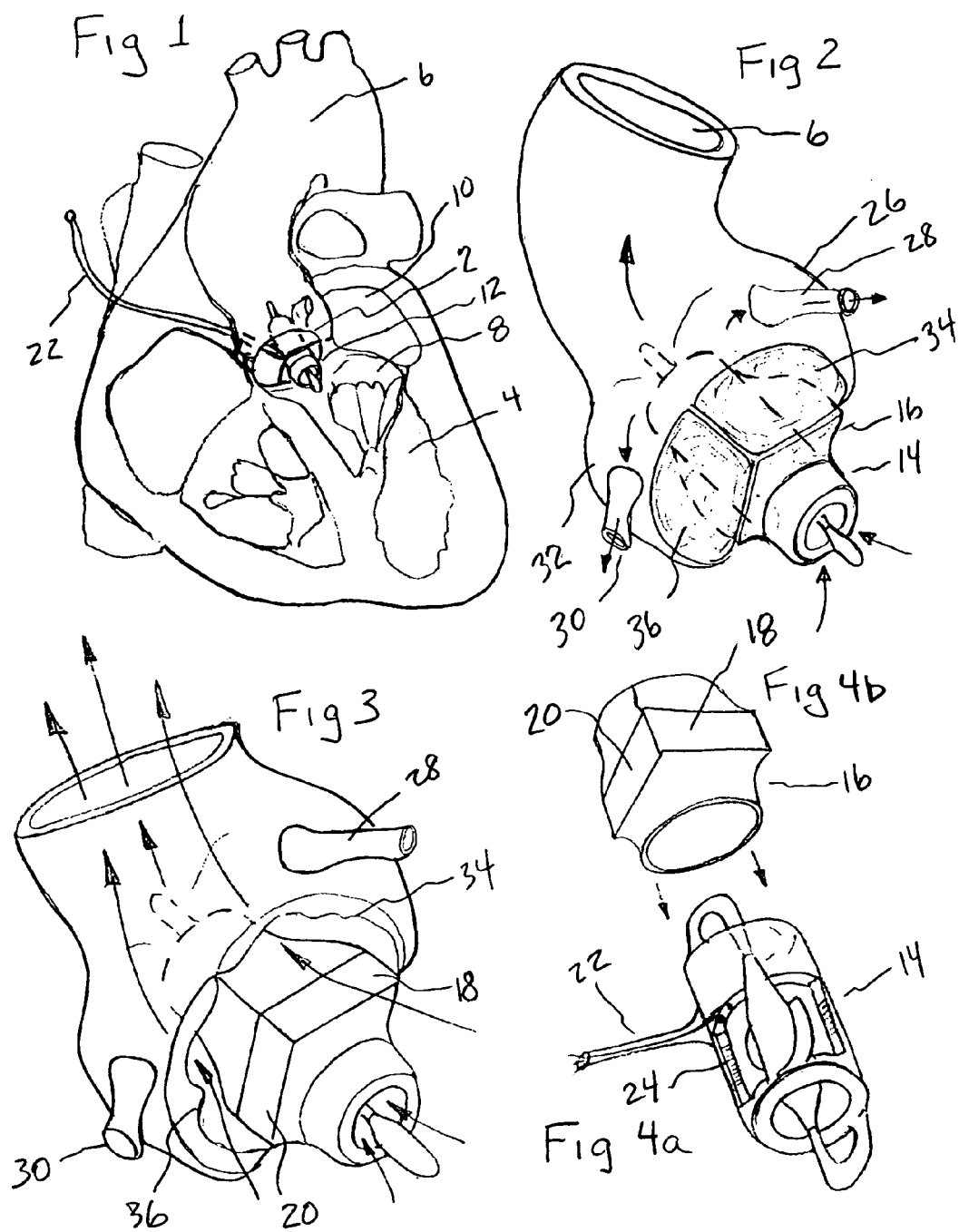

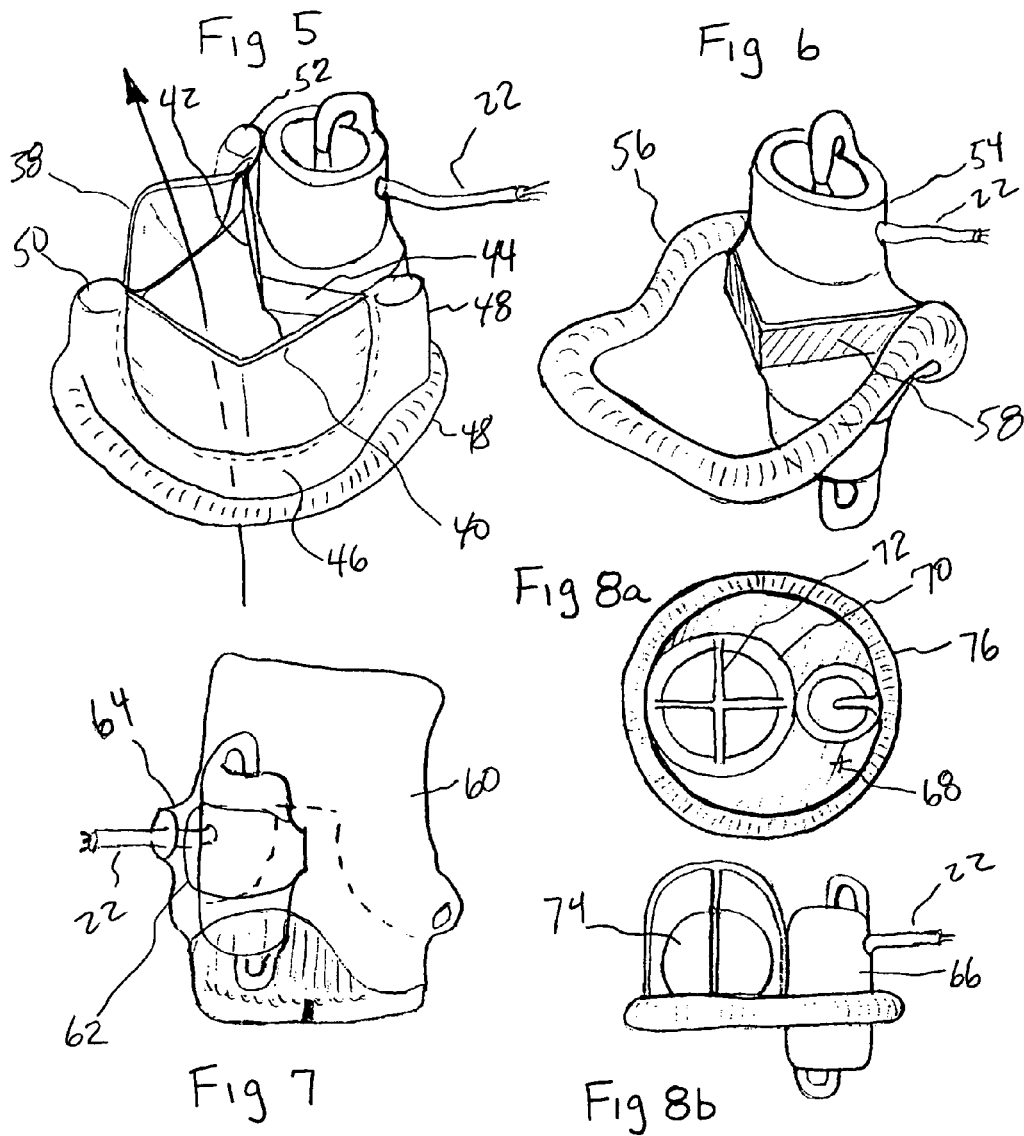

MINIMALLY INVASIVE TRANSVALVULAR VENTRICULAR ASSIST DEVICE

BACKGROUND OF THE INVENTION

Mechanical circulatory support devices have gained increasingly common use in end stage heart failure patients. Presently, more than a thousand patients per year are treated with implantable ventricular assist devices (VADs), as bridge to transplant, bridge to recovery, or for permanent use. The pusher plate and other types of positive displacement pumps approved by the FDA are large, heavy, and generally noisy devices which have major limitations, including poor reliability and a high incidence of serious adverse events such as bleeding, infection, thromboembolism, and stroke. Over the past five years, rotary blood pumps have been undergoing clinical trials in the United States, or have received CE mark approval for use abroad. The Jarvik 2000 intraventricular axial flow pump VAD, has been used in over 100 patients, and has supported a patient almost five years, longer than any other single VAD of any type. One patient has survived for over 6 years with the old type positive displacement pump, but only after his original implant device wore out and it was replaced with a new one.

Although rotary blood pumps of many designs represent a very promising improvement over the old generation positive displacement VADs, none has yet reduced the incidence of serious adverse events to a practically negligible rate. Published data indicates that the three month mortality with all types of VADs remains at approximately 20-30%, a rate which is only acceptable in patients facing the risk of imminent death at the time of surgery. Many experts in the field recognize that early mortality is increased if the VAD is not used until the last minute, when the patient's deterioration is advanced. Earlier application of the less invasive rotary blood pumps holds promise to reduce early mortality, but no device developed to date has been recognized by surgeons, cardiologists, and the public as a true "breakthrough device" appropriate to implant in NYHA class III patients, who have serious heart failure but are not yet facing a risk of imminent death.

No heart assist device is better than its worst characteristic. If everything were perfect except the durability were less than two years the device would have limited usefulness for permanent implantation. If it were durable for decades but had a very high incidence of serious infection, it would find limited use. If it had excellent long term freedom from failure and no serious adverse events, but required highly invasive surgery, with high surgical mortality and prolonged post implant hospitalization, it would not be widely accepted.

Experience teaches that each and every level of device complexity brings potential problems, and ultimate simplification is the best approach to solve all limiting problems. Experience also teaches that despite the greatest care to prevent damage to external components, such as batteries, cables, and connectors, and despite concerted efforts to educate patients and caregivers in proper daily use, damage, mistakes, and oversights can never be completely avoided. Therefore, the safest VAD is one which is designed to permit it to be safely turned off for at least enough time to replace external components with backup equipment.

Regarding complexity, almost all VADS have significant problems associated with the inflow and outflow conduits used to connect the devices to the circulatory system. The Jarvik 2000 avoids the need for any inflow cannula, because the pump is placed directly inside the ventricle. But it still requires an outflow graft which must be sutured to the aorta and has been the site of bleeding complications. The present invention eliminates both the inflow cannula and the outflow graft. Only one other type of device does this, a pump placed within the outflow valve orifice, disclosed by Yozu in U.S. Pat. No. 4,994,017, and further described in scientific publications such as "The valvo-pump, an axial blood pump implanted at the heart valve position: concept and initial results." 1: Artif Organs. 1992 June; 16(3):297-9. Despite elimination of the inlet and outlet cannulae, pump placement within the entire valve orifice, as disclosed in the prior art, has significant disadvantages. If the pump stops, the patient's natural heart has no valved outlet, and therefore it cannot pump effectively to support the patient even for a short time. If an axial pump with a large cross sectional flow area is used, there will be massive aortic regurgitation and the natural heart will fail. If an axial pump with a small cross sectional flow area is used, there may be little regurgitation, but there will be high resistance and the natural heart will not be able to eject sufficient blood.

In the present invention, the axial flow pump is only placed in one third of the valve area, and the other two thirds of the area is a functional valved outflow channel. The axial flow pump may be designed with a small cross sectional flow area, in which case regurgitation will be minor, and the natural heart will pump effectively.

The degree of miniaturization made possible by the present invention is dramatic compared both to the "old model" pusher plate pumps such as the HeartMate or Novacor, and even compared to the smallest rotary blood pumps in clinical trials, i.e. the Jarvik 2000, the MicroMed DeBakey VAD, and the HeartMate II, which are all more than ten times the size and weight of the transvalvular device disclosed herewithin.

The preferred embodiment of transvalvular pump of the present invention displaces only 2.5 cc of volume and weighs only 8 grams. At 1,800 grams the Novacor weighs 225 times as much. At 1,200 grams, the HeartMate weighs 150 times as much. At 340 grams the HeartMate II weighs 42 times as much. At 112 grams the Micromed VAD weighs 14 times as much, and at 85 grams the Jarvik 2000 weighs 10 times as much. At 25 cc the Jarvik 2000 is the smallest permanent VAD in clinical use, and it is still ten times as large as the transvalvular device of the present invention.

This degree of miniaturization far surpasses any known permanently implantable heart assist device in the prior art, and enables minimally invasive surgical techniques that are not otherwise possible.

Other inventions disclosed in the prior art utilize small axial flow pumps placed beyond the aortic valve with the valve left in place, such as Nash, U.S. Pat. No. 4,919,647, "Aortically located blood pumping catheter and method of use" and Pasque, U.S. Pat. No. 5,290,227, "Method of implanting blood pump in ascending aorta or main pulmonary artery". If these pumps stop, the aortic valve will still function, so the natural heart can sustain the patient. However, by placing the pump above the openings to the coronary arteries, the pressure in the coronary arteries is reduced to intraventricular pressure during diastole (~5 mmHg), which is detrimental to coronary artery flow, rather aortic diastolic pressure (~70 mmHg), which is necessary to provide normal coronary artery flow.

One basic distinguishing characteristic of the present invention compared to some prior art inventions using axial pumps at the aortic position or just distal to it, is that the pump is placed in parallel with the natural heart rather than in series as in Yozu, Nash, and Pasque.

Another prior art approach using miniature axial flow pumps near the aortic valve is disclosed by Barbut in U.S. Pat. No. 6,136,025, "Endoscopic arterial pumps for treatment of cardiac insufficiency and venous pumps for right-sided cardiac support". The pump may be placed across the aortic valve, with a balloon surrounding it to occlude the aorta, effectively producing a series configuration. If no balloon is used, the pump may lie in a cannula across the aortic valve and function in parallel, similar to the arrangement with the Wampler in U.S. Pat. No. 4,625,712 "High-capacity intravascular blood pump utilizing percutaneous access", Jarvik in U.S. Pat. No. 5,888,241 "Cannula pumps for temporary cardiac support and methods of their application and use", and by Rau in U.S. Pat. No. 6,176,848 "Intravascular blood pump". However, in any pump where a cylindrical cannula is passed through the central portion of the aortic valve and the leaflets must seal against the cannula, the shape of the valve leaflets does not exactly match the cannula. Also, there is motion of the cannula relative to the valve. These factors make the valve leaflets subject to erosion if the cannula is left in place long term. In the present invention, the device is designed with non-cylindrical facets that properly match the configuration of the closed valve leaflets to avoid erosion, and the pump is fixed in position relative to the leaflets. The faceted surfaces upon which the tissue valve leaflets seal may be covered with natural tissue, such as a portion of the natural valve leaflet of the patient or treated pericardium, to minimize erosion to the functioning valve leaftets. In another embodiment, a mechanical heart valve and miniature blood pump are combined and implanted at the aortic annulus. The mechanical valve may use one or more rigid pivoting leaflets, flexing polymer leaflets, or a confined mechanical occluder such as a valve ball.

OBJECTS OF THE INVENTION

1. It is an object of the present invention to provide a highly miniaturized and effective heart assist device able to be implanted by minimally invasive surgical techniques.

2. It is also an object of the present invention to provide a miniature blood pump for treatment of heart failure which may be permanently implanted across a portion of the aortic or pulmonary valve annulus while maintaining function of an outflow valve in the natural valve position.

3. It is another object of the invention to provide a miniature heart assist device which requires neither an inlet nor an outlet cannula.

4. An additional object of the invention is to provide a miniature transvalvular pump which preserves the function of two of three of the patient's natural outflow valve leaflets with excellent sealing and minimal leaflet wear or erosion.

5. A further object of the invention is to provide a transvalvular pump custom matched to the individual patient's anatomy for optimal performance.

6. Another object is to provide a transvalvular pump which may be safely turned off in patients who have diminished residual natural heart function.

7. A still further object of the invention is to provide a combination of a transvalvular blood pump and an outflow valve as a single surgically implantable unit, to facilitate implant surgery.

8. An additional object of the invention is to provide a truly non-thrombogenic permanently implantable blood pump which is washed by high blood flow on its outer surfaces as well as its inner surfaces.

9. Another object of the invention is to provide a miniature axial flow blood pump with durability exceeding a decade, that is small enough to fit mostly within the area occupied by the non-coronary sinus of the aortic valve, and that projects only a short distance into the outflow tract of the left ventricle.

THE DRAWINGS

FIG. 1 is a view showing the natural heart cut open with a transvalvular pump implanted into the non-coronary cusp of the aortic valve.

FIG. 2 is a view of the isolated aorta and aortic valve, with the valve leaflets closed, showing the positioning of the pump in place of one leaflet.

FIG. 3 is a view of the aortic root and aortic valve with a transvalvular pump implanted and with the two remaining aortic leaflets open.

FIG. 4a is a partially cutaway view of a generally cylindrical axial flow pump which mounts within the anatomically shaped cusp adaptor as shown by the arrows.

FIG. 4b is a three dimensional drawing of the anatomically shaped cusp adaptor which must be affixed to the pump shown in FIG. 4a to obtain the complete functional transvalvular ventricular assist device as illustrated in FIG. 3.

FIG. 5 is a three dimensional drawing of a stented tissue valve or polymer leaflet valve shown in the leaflet open position, with an integrally attached transvalvular VAD.

FIG. 6 is a three dimensional drawing of a transvalvular VAD integrally attached to an anatomically shaped semi-rigid sewing cuff, adapted to be sutured into the aortic annulus.

FIG. 7 is a schematic drawing of a transvalvular VAD mounted within a stentless allograft or homograft with the power cable of the VAD exiting through the remnant of a coronary artery.

FIG. 8a is a top view of the combination of a transvalvular VAD and a mechanical heart valve shown in FIG. 8b, mounted within the same sewing ring.

FIG. 8b is a side view of a transvalvular VAD and a mechanical valve mounted within a sewing ring, with the ball valve shown in the closed position.

SPECIFIC DESCRIPTION OF THE INVENTION

The present invention provides a miniature blood pump which fits within the cross sectional area of one of the three leaflets of either the aortic or pulmonary valve, with the pump inlet side having unobstructed communication with the ventricular cavity and the pump outlet located in the aorta or pulmonary artery distal to the valve leaflets. Referring to FIG. 1 which is a cut away drawing of the heart with the anterior portion of the left and right ventricles removed, the aortic valve 2, is located between the left ventricle 4, and the aorta 6. The mitral valve 8, is located between the left ventricle 4, and the left atrium 10. A transvalvular VAD 12, is implanted into the non-coronary sinus of the aortic valve, which is located adjacent to the mitral valve 8. In the preferred embodiment it is comprised of a miniature axial flow pump 14, best seen in FIG. 4a, and a shaped anatomic adaptor 16, best seen in FIG. 4b. The anatomic adaptor has two facet like surfaces 18, 20, that match the size and shape of the sealing surfaces of the two valve leaflets that close against them. Preferentially, the anatomic adaptor is fabricated of a soft biocompatible elastomer such as silicone rubber, and is able to be placed tightly over axial pump 14, and retained there by an interlocking boss within the bore of the adaptor (not shown) and a groove (not shown) on the outside surface of the axial pump. Alternatively, bonding or another retaining method may be used, and the adaptor may be fabricated of a rigid material such as titanium. The adaptor also may have a hole or slot to permit the power cable 22, which supplies electricity to the pump motor 24, to pass through it.

Referring to FIG. 2, the aortic root and aortic valve are shown. The aortic root has three bulges each called a sinus of valsalva. One of these 26, is the location from which the left main coronary artery 28, branches off from the aorta. The opening in the sinus of valsalva into the coronary artery is called the coronary osteum. The right coronary artery 30, branches off the aorta from another sinus of valsalva. The transvalvular VAD is placed in the third sinus of valsalva which has no coronary artery originating from it. This is the preferred location for the VAD, because nothing may be placed so as to obstruct a coronary artery which would cause a major heart attack. The sinus which lacks a coronary osteum is called the non-coronary cusp. It is this "non-coronary" leaflet which is removed to make an opening for the transvalvular VAD. Alternatively, a hole may be cut in this leaflet, through which a portion of the inlet side of the device may be passed, while securing the remaining portion of the leaflet over the anatomical adaptor. In this way, the portion of the leaflet remaining includes the part normally making contact with the other two leaflets, and when the valve is closed the leaflets contact only leaflet tissue. This helps avoid erosion of the leaflets.

When used to support the right ventricle, a transvalvular VAD may be placed in any of the three sinuses of the pulmonary valve, which has no coronary arteries originating there. Nonetheless, it is best to remove the most anterior leaflet of the pulmonary valve in order to avoid compressive obstruction of the coronary venous return into the right atrium.

Still referring to FIG. 2, valve leaflets 34 and 36, are shown in the closed position, bulging towards the left ventricle. This occurs during the portion of the cardiac cycle called diastole, when the ventricular cavities are filling with blood. Valve leaflets 34 and 36 seal against faceted surfaces 18 and 20 preventing blood from the aorta from flowing back into the heart. The optimal shape for the anatomic adaptor 16, fills the complete sinus of valsalva in which it is placed, with no crevices where blood clots can form. The adaptor shape nests into the sinus of valsalva and helps retain the miniature blood pump in place, and also helps hold the facet like valve sealing surfaces in exact opposition to the closed valve leaflets. In one embodiment of the invention, where the patient's natural valve leaflets are preserved, this shape is based on custom geometric measurements from CT or MRI imaging of the individual patient's natural valve. Since it is anticipated that most cases in which transvalvular VADs will be used will be elective implants in non-emergency cases, there is time to custom fabricate the adaptor piece to exactly fit the patient.

As shown by the arrows in FIG. 2, blood is pumped from the left ventricle into the aorta through the transvalvular axial flow pump during diastole. Blood from the aortic root enters the coronary arteries. During systole, the portion of the cardiac cycle in which the ventricles contract and eject blood, the axial pump continues to pump blood into the aorta, as shown by the arrows in FIG. 3, which also illustrates the open position of the valve leaflets 34, 36, during systole. Flow passes across the outer surface of the pump and adaptor washing them thoroughly to prevent thrombus formation on their surfaces. The only portion of the outer surface of the device that is not washed is the portion resting against the wall of the aortic sinus. In this area of the device, a porous surface may be provided to promote tissue in-growth and bio-integration of the prosthetic device into the natural tissue of the aorta. Thus it is apparent that the invention provides not only a cardiac assist pump to augment flow from the heart, but also provides a unique and optimal structure to avoid thrombus formation.

FIG. 5 illustrates an embodiment of the invention in which the transvalvular VAD (shown with the valve leaflets open) is manufactured as a unit which includes a stented two leaflet tissue or polymeric valve. Valve leaflets 38 and 40 seal against faceted surfaces 42, 44, of the VAD adaptor. The stent 46, includes three arms supporting the valve leaflets 48, 50, 52, and a sewing cuff 48. This permits the combined valve/VAD device to be surgically implanted with nearly the identical technique used for a stented tissue valve. One additional step in the surgical technique is needed. A short length of small diameter vascular graft is sutured to the non-coronary sinus to create what appears to be a coronary osteum leading to a graft. The power cable of the pump is passed through this and when the valve is seated, the graft is tied around the cable forming a seal to prevent bleeding where the cable exits the aorta.

FIG. 6 shows a transvalvular VAD 54, manufactured with an attached semi-rigid sewing cuff 56 anatomically shaped to permit implantation within the aortic root while retaining two of the patient's natural leaflets. A strip of biologic tissue 58, such as pericardium is affixed to the facet like surfaces against which the valve leaflets seal. Other shapes and positions of sewing cuffs or suture holding pads may be provided to anchor the transvalvular VAD in place without departing from the spirit of the invention.

FIG. 7 illustrates the combination of a transvalvular VAD with a stentless aortic valve. The stentless prosthesis includes a section of human or animal aorta, 60 which contains the natural valve leaflets as well as each sinus of valsalva and short stumps of the coronary arteries which are typically tied off. In the optimal version of this iteration, a custom made anatomic adaptor 62, is fabricated to match the geometry of the tissue leaflets when closed by pressurization of the aorta. Imaging methods and manufacturing methods including stereolithography and CAM may be used to construct a uniquely shaped adaptor for each individual tissue valve, thus giving optimal leaflet fit. After the needed images are made and the adaptor fabricated, one leaflet is removed, and the VAD is attached in place passing the power cable through a coronary artery 64, and tying a ligature around it to seal the cable. This then may be implanted with the same technique used to implant a standard stentless aortic valve.

FIGS. 8a and 8b illustrate a embodiment of the present invention in which the transvalvular VAD is combined with a mechanical heart valve. For simplicity of illustration, a ball valve has been shown. The ball valve geometry gives a rather small opening area when combined with the pump and would be a sub-optimal design. Many other mechanical valve designs could be used, including tilting disc valves and bi-leaflet valves which would be superior. The axial pump 66, is fixed so as to pass through a disc, 68, which also supports a valve seat 70, that in turn supports the arms of a ball valve cage 72. The valve ball 74 is confined in the cage and functions as in a usual ball valve. The sewing cuff 76, permits implantation with a technique similar to the surgical method described for the device of FIG. 5 above.

The information disclosed in the description of the present invention is intended to be representative of the principles I have described. It will thus be seen that the objects of the invention set forth above and those made apparent from the preceding description are efficiently obtained and that certain changes may be made in the above articles and constructions without departing from the scope of the invention. It is intended that all matter contained in the above description and shown in the accompanying drawings shall be interpreted as illustrative but not in a limiting sense. It is also understood that the following claims are intended to cover all of the generic and specific features of the invention herein described and all statements of the scope of the invention which, as a matter of language, might be said to fall there between.

I claim:

1. A miniature blood pump having outer faceted surfaces approximating the geometry of the sealing portion of a natural outflow (aortic or pulmonary) valve leaflet, said blood pump incorporating a rotating impeller and adapted to be implanted in the outflow tract and across the outflow valve of the left or right ventricle at the position where one leaflet of the natural valve has been surgically removed or pierced, such that the remaining two leaflets of the natural valve seal against said faceted surfaces.

2. The miniature blood pump of claim 1 in which said faceted sealing surfaces are covered with biological material such as pericardium, or collagen.

3. The miniature blood pump of claim 1 in which said faceted sealing surfaces are covered with a smooth wear resistant polymer layer.

4. The pump of claim 1 in which said faced surfaces are manufactured to exactly fit the size and shape of the remaining two leaflets of the individual patient's natural valve, utilizing computer manufacturing methods based upon imaging data which measures the three dimensional configuration of the individual patient's valve.

5. A miniature blood pump and ventricular outflow valve, configured to function in parallel with said blood pump, mounted together upon a ring of rigid or flexible material for suturing at the position of the aortic or pulmonary valve, said blood pump incorporating a rotating impeller.

6. The device of claim 5 in which said valve is a tissue valve.

7. The device of claim 5 in which said valve is a prosthetic polymer leaflet valve.

8. The device of claim 5 in which said valve is a mechanical ball valve.

9. The device of claim 5 in which said valve is a mechanical tilting disc valve.

10. The device of claim 5 in which said valve is a mechanical bi-leaflet valve.

11. The device of claim 5 in which said valve is an allograft or homograft, said device having two faceted faces against which two leaflets of said tissue valve seal when closed, and said faceted surfaces are manufactured to closely fit the size and shape of the leaflets of the allograft or homograft used in each individual device, utilizing computer manufacturing methods based upon measurements of the three dimensional configuration of the individual valve.

12. A cardiac assist device comprising a miniature generally cylindrical axial flow pump supported within an anatomically shaped adaptor, said adaptor fabricated to closely fit the size and shape of one cusp of the aortic or pulmonary valve and help retain said cardiac assist device in place.

13. The cardiac assist device of claim 12 in which the shape of said adaptor is matched to the anatomy of the individual patient based on high resolution imaging of the patients aorta or pulmonary artery.

14. The method of assisting the pumping function of the heart comprised of removing or piercing one leaflet of the aortic or pulmonary valve, without removing or piercing the remaining two leaflets of said valve, and positioning a miniature axial flow blood pump directly across the valve, with no inlet or outlet cannula, such that blood is pumped from the ventricle directly into the aorta or pulmonary artery.

* * * * *